United States Patent [19]

Grinblat

[11] Patent Number: 5,535,060
[45] Date of Patent: * Jul. 9, 1996

[54] OPTICAL STEREOSCOPIC MICROSCOPE SYSTEM

[76] Inventor: Avi Grinblat, 25 Central Park West - Apt. 4V, New York, N.Y. 10023

[ * ] Notice: The term of this patent shall not extend beyond the expiration date of Pat. No. 5,438,456.

[21] Appl. No.: 380,602

[22] Filed: Jan. 30, 1995

Related U.S. Application Data

[63] Continuation of Ser. No. 907,676, Jul. 2, 1992, Pat. No. 5,438,456, which is a continuation-in-part of Ser. No. 651,788, Feb. 7, 1991, abandoned.

[51] Int. Cl.⁶ .............................. G02B 5/04; G02B 21/22
[52] U.S. Cl. ........................... 359/835; 359/368; 359/376
[58] Field of Search ...................... 359/368, 376, 359/380, 642, 708, 728, 831–836; 351/160 R, 219

[56] References Cited

U.S. PATENT DOCUMENTS

| | | | |
|---|---|---|---|
| 1,716,321 | 6/1929 | Pearson . | |
| 2,660,090 | 11/1953 | Leitz, Jr. et al. | 359/835 |
| 3,482,906 | 12/1969 | Volk | 351/219 |
| 4,157,859 | 6/1979 | Terry . | |
| 4,518,231 | 5/1985 | Huchel et al. | 359/377 |
| 4,521,083 | 6/1985 | Togino | 359/656 |
| 4,571,038 | 2/1986 | Jako | 359/376 |
| 4,640,586 | 2/1987 | Iba et al. | 359/656 |
| 4,640,595 | 2/1987 | Volk | 351/160 R |
| 4,666,256 | 5/1987 | Shimizu et al. | 359/658 |
| 4,710,000 | 12/1987 | Spitzens et al. | 351/205 |
| 4,723,842 | 2/1988 | Twisselman et al. | 359/836 |
| 4,728,183 | 3/1988 | Heacock et al. | 351/219 |
| 4,763,968 | 8/1988 | Minami et al. . | |
| 4,802,749 | 2/1989 | Togino et al. | 359/377 |
| 4,838,671 | 6/1989 | Papritz et al. | 359/835 |
| 5,009,487 | 4/1991 | Reiner | 359/831 |
| 5,046,836 | 9/1991 | Volk | 351/219 |
| 5,438,456 | 8/1995 | Grinblat | 359/376 |

FOREIGN PATENT DOCUMENTS

| | | | |
|---|---|---|---|
| 3507458 | 9/1986 | Germany | 351/219 |
| 89C20359 | 5/1989 | Germany . | |
| 2233780 | 1/1991 | United Kingdom | 359/504 |

OTHER PUBLICATIONS

Design Of Fire Control Optics ORDM 2–1, Sec. 103, p. 295.

*Primary Examiner*—Thong Nguyen
*Attorney, Agent, or Firm*—Eliot S. Gerber

[57] ABSTRACT

A stereoscopic microscope system is adapted for vitrectomy eye surgery. A conformer lens positions the eye being operated upon and an aspherical lens system, adjacent the conformer lens, produces an inverted image. That image is reinverted by a prism system having two pairs of prisms, each pair being an Abbe's Modification of Porro prism system. Each prism of the prism system has the same size and shape and the prisms are cemented together to form a unitary prism cluster.

15 Claims, 5 Drawing Sheets

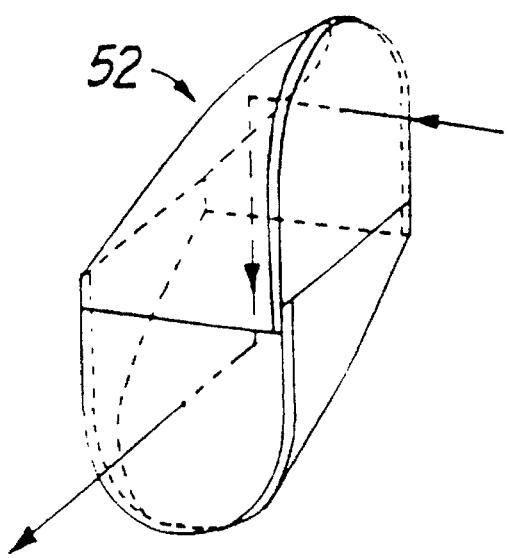
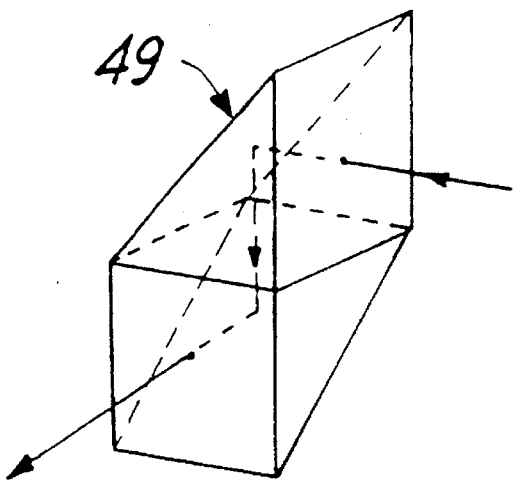
FIG.3A　　　　　　FIG.3B
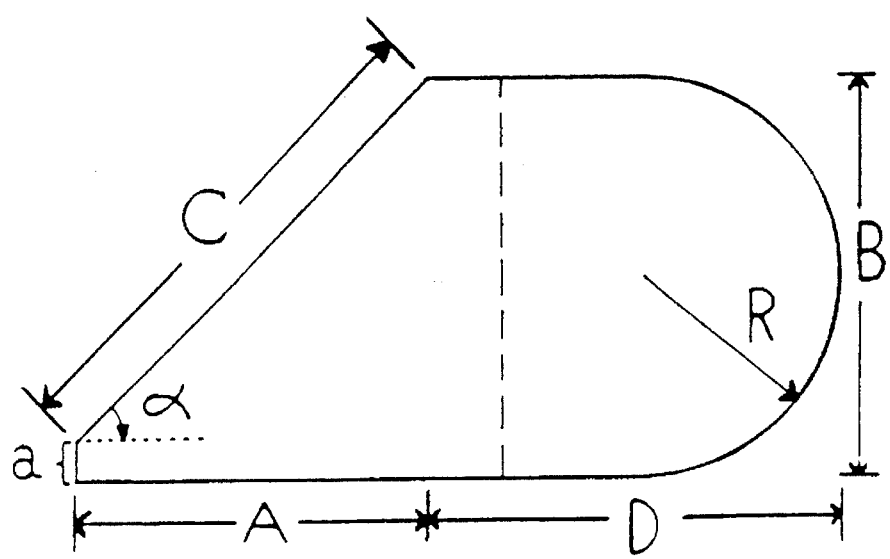
FIG.3C

OPTICAL STEREOSCOPIC MICROSCOPE SYSTEM

FIELD OF THE INVENTION

The present invention relates to optical microscope systems and more particularly to optical bright-field stereoscopic microscope systems used in connection with microsurgery medical procedures.

This application is a continuation application based upon application Ser. No. 07/907,676, filed Jul. 2, 1992, now U.S. Pat. No. 5,438,456, issued Aug. 1, 1995, which was a continuation-in-part application partly based on application Ser. No. 07/651,788 filed Feb. 7, 1991 and entitled "Optical Stereoscopic Microscope System" now abandoned.

BACKGROUND OF THE INVENTION

At the present time, optical, bright-field, stereoscopic microscopes are used in connection with medical surgical procedures, for example in the microsurgery of the eye. Such microscopes have two eyepieces so that the viewer may view the object to be magnified using both his eyes at the same time. The viewer sees two side-by-side, magnified images of the object and produces a three-dimensional ("3D") image in his mind.

In the conventional stereoscopic microscope the individual images, and the resulting 3-D image, are not inverted. The viewer sees an image which is, in effect, in the same position as the object.

However, in some surgical procedures, especially in inner eye surgery or "vitrectomy surgery" for the back area of the retina, an additional magnifying lens system is positioned between the stereoscopic microscope and the object, i.e. the eye being operated upon. That additional lens system may invert the image so that the surgeon sees a mirror image. This presents a difficult problem for the surgeon in eye-hand coordination. Also, such inverted images may be presented in certain digital diagnostic systems.

German Gebrauchsmuster G3902035.9 of May 11, 1989, discloses a stereoscopic optical microscope in which the two images are inverted by complex mirror and prism arrangements. Each of the images is reflected from a prism to a first mirror, then to a second mirror and then to another prism. Each time the image moves through an air gap, from the prism to the mirror or from one mirror to another, it necessarily loses at least 6% in light, and therefore in clarity. Consequently, each image is degraded at least 18% by the inversion prism-mirror system of the German Gebrauchsmuster.

SUMMARY OF THE INVENTION

In accordance with the present invention, there is presented an improved optical stereoscopic microscope system. The system utilizes a conventional stereoscopic microscope which preferably has lenses for direct viewing by a viewer as well as auxiliary lens systems for stereo photography, stereo camcorder or video cameras.

An additional lens system is used directly above the object to be viewed, for example, near to the eye which is undergoing surgery. That additional lens system presents a wide and magnified image, which is especially useful in eye surgery. The additional lens system is an aspherical optical lens system and a contact conformer lens. The aspherical lens system produces an inverted image of the object being viewed. That image is again inverted to present a non-inverted image to the viewer, by two prism systems, one for each eyepiece of the stereoscopic microscope. The prisms are of a special design called "Abbe's Modification of the Porro Prism System" in which the image is internally inverted, by the prisms, without air gaps and without mirrors. The image is not degraded by the internal prism inversion as it does not pass through a prism-mirror or mirror-mirror air gap.

The prism system consists of two pairs of each of two prisms for a total of four prisms which are cemented together.

OBJECTIVES AND FEATURES OF THE INVENTION

It is an objective of the present invention to provide an optical stereoscopic microscope system, especially adapted for eye microsurgery, in which the user sees the objects without inversion of the image.

It is a further objective of the present invention to provide such a microscope system in which the inversion is accomplished without appreciable loss of light, i.e. without appreciably degrading the image and the inversion device is relatively simple, low in cost and available for ready removal from the optical paths of the microscope.

It is a feature of the present invention to provide a stereoscopic microscope system which is adapted for microsurgery, for example to be used by vitreous surgeons. The system includes positioning means to position the object to be viewed and an aspherical lens system adjacent the positioning means. The aspherical lens system may be constructed in two primary ways. The aspherical lens system may include a first lens having convex-concave curved faces proximate the positioning means and a second lens having convex-concave curved faces and facing the first lens. The concave faces of the first and second lenses face each other and the aspherical lens system produces an inverted image. Alternatively, the aspherical lens system may be one solid lens with two oppositely facing convex curved faces to produce an inverted image. The inverted image from the aspherical lens system may then be split into two inverted images by either an objective lens or a zoom lens of the stereomicroscope. Next, a prism system inverts the two separated and inverted images from the aspherical lens system. That prism system consists of two pairs of prisms, each pair of prisms being an Abbe's Modification of Porro Prism System. Binocular tubes and eyepiece means, which may be conventional, enlarges each of the reverted images from the prism system.

Preferably, the microscope means includes a zoom optical system and a beam splitter, and the prism system is positioned between the zoom optical system and the beam splitter.

BRIEF DESCRIPTION OF THE DRAWINGS

Other objectives and features of the present invention will be apparent on the following detailed description taken in conjunction with the accompanying drawings.

FIGS. 3A and 3B are perspective views of single prisms of varying geometries;

FIG. 3C is a side plan view of the prism of FIG. 3A;

DETAILED DESCRIPTION OF THE INVENTION

Figure 1:
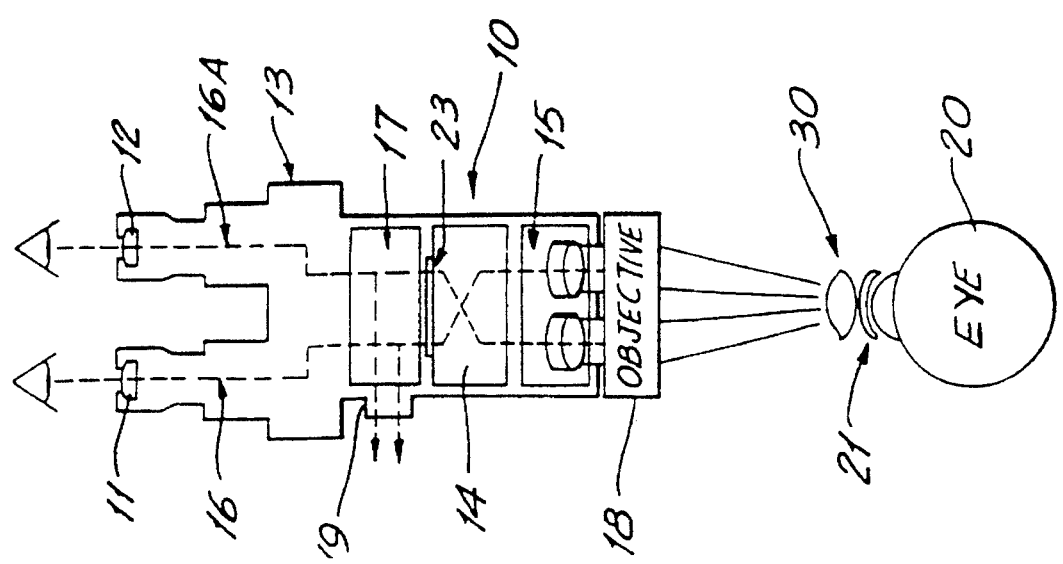
FIG. 1 is a side cross-sectional view, showing the optical stereoscopic system of the present invention.

FIG. 1 shows the stereo microscope system 10 of the present invention. The microscope itself may be a conventional optical stereo microscope available, for example, from Nikon, Canon or Wild-Leitz.

The system includes a left eyepiece lens 11 and a right eyepiece lens 12 within the housing 13. A zoom lens system 15, which may be conventional, is used to enlarge or reduce the images received from the objective lens system 18. The zoom lens 15 uses two image beams which eventually become the left optical image 16 and the right optical image 16A. However, the two image beams from the zoom lens 15 are first sent through an inverter 14 (inverter prism system), described in detail below, which switches (inverts) the left and right image beams. A conventional beam amplifier 17 sends these inverted image beams to the eyepieces 11 and 12, as well as to an additional optical viewing device 19, such as a video camera or assistant's eyepiece.

Except for the inverter 14 the stereo microscope is conventional.

Figure 6:
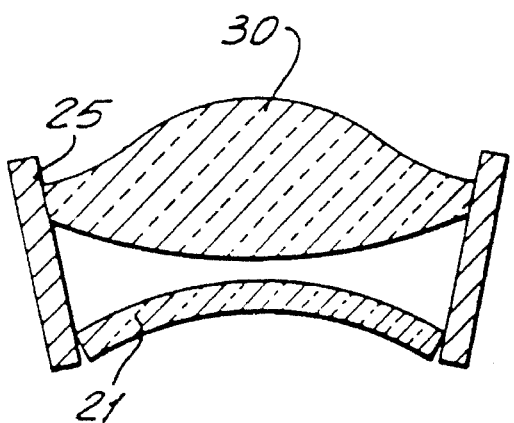
FIG. 6 is a side cross-sectional view showing an aspherical lens and a cornea conformer lens contained in a single housing.

An "additional aspherical lens system" 30 is positioned near the object and below the objective lens system 18. The additional lens system 30 presents a magnified and inverted image of the object 20. The object 20 is shown as being an eye undergoing microsurgery. A non-magnifying conformer lens 21 (primary contact element) is used in contact with the eye's cornea to cause the cornea, by slight pressure, to have a uniform shape, namely the shape of that face of lens 21 which is in contact with the cornea. Conformer lens 21 acts as the positioning means to position the eye which is to be viewed. As shown in FIG. 6, the aspherical lens 30 and the conformer lens 21 may be contained in a common housing 25 when used in eye surgery.

The inverter 14 (inverter prism system) consists of two prism systems 50 and 70. The prism system 50 takes the left image and inverts it and transmits it to the right eyepiece. The prism system 70 takes the right image, inverts it and transmits it to the left eyepiece.

Figure 3D:
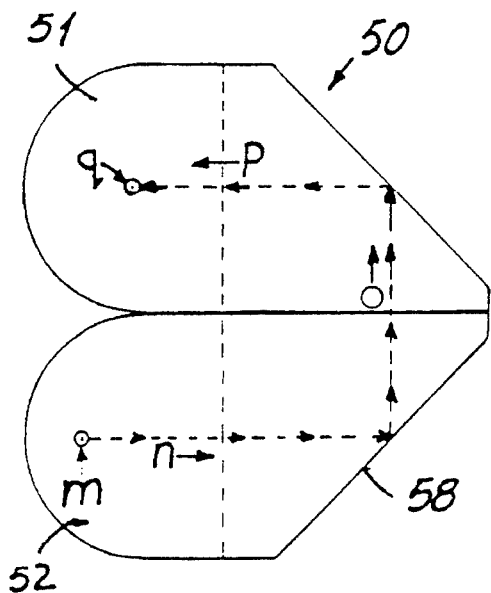
FIG. 3D is a side plan view of one pair of the prisms of FIG. 3A.
Figure 3E:
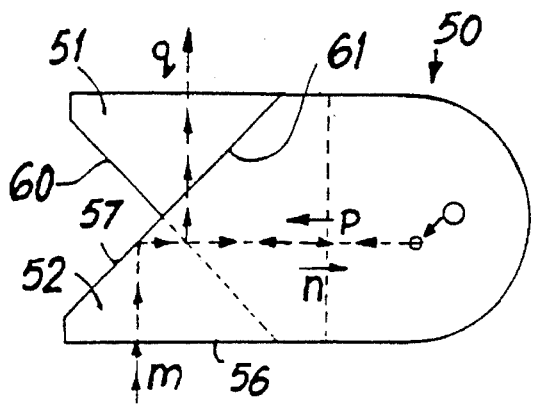
FIG. 3E is a top plan view of one pair of the prisms of FIG. 3A.

For simplicity of explanation FIGS. 3D and 3E show a single pair of prisms forming prism system 50. The prism system 50 inverts the image. Since the additional lens system 30 has inverted the image, relative to the object, the prism system 50 inverts the image again to present a non-inverted image to the eyepiece lens of the microscope. The prism system 50 is called "Abbe's Modification of the Porro Prism System" ("Abbe-Modification"). The basic Porro prism system consists of two right-angle prisms identical in construction and placed at right angles to each other. The Abbe-Modification prism system 50 consists of two prisms 51 and 52 which are identical. Each of the four prisms 51–54 forming the prism cluster of inverter 14 are exactly the same, in size, shape and optical properties. The prisms 51–54 may all be left prisms or may all be right prisms.

As seen in FIGS. 3D and 3E, the optical image beam m enters from the bottom face 56 of prism 52 and is reflected from a 45° angles face 57 to become beam n, which is reflected from a 45° angle face 58 (FIG. 3D) to exit, as beam o, from the side of the prism 52.

That beam o enters the second prism 51 of the pair and is again internally reflected twice and exits the top of prism 51. The entry and exit beams, to the prism pair, are parallel but not aligned.

The following is a chart of relative dimensions for each of the prisms 51–54: A=1.00 (length of face 58); n=1.517; α=45°; a=0.10 (chosen arbitrary); B=A+a=1.10; C=1.4142× A=1.4142; D=A+2a=1.20; R=B/2=0.55; Δ=B=1.10; d=2 (2A+3a)=4.60; and d/n=3.0323.

Preferably each of the prisms 51–54 have the following dimensions: B=21 mm=Δ; R=10.5 mm; a=2 mm; A=19 mm; α=45° C.; C=26.869 mm; n=28.823; D=23 mm; d=88 mm; and d/n=3.053.

Figure 3F:
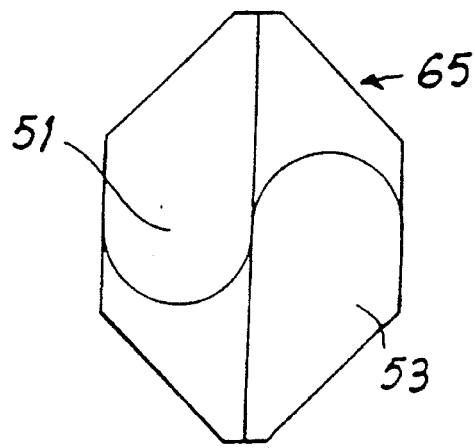
FIG. 3F is a top view, showing the top layer of two pairs of the prisms of the inverter.
Figure 3G:
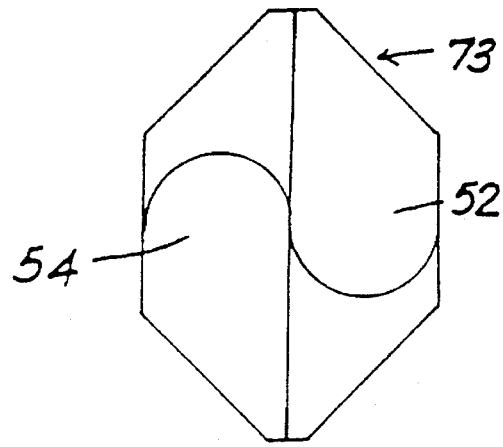
FIG. 3G is a bottom view, showing the bottom layer of two pairs of the prisms of the inverter.

The prisms 51 and 53 are cemented together to form top layer 65 and the prisms 52 and 54 are cemented together to form bottom layer 73, as shown in FIGS. 3F and 3G.

The faces of prism 52 are shown in FIGS. 3A–3D. Each of the other three prisms are identical. The face 58 having dimensions C and 2R is one of the two reflective 45° faces of the prism. Preferably, but not necessarily, faces 60, 61 (the entry and exit faces) are reflective (silvered).

Figure 4A:
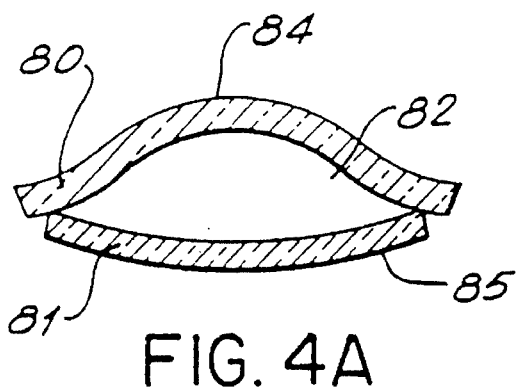
FIG. 4A is a side cross-sectional view, showing the aspherical lens system comprised of two lenses.

The additional aspherical lens system comprised of two lens are shown in FIG. 4A. It consists of a top convex-concave lens 80 and a bottom concave-convex lens 81. The bottom lens 81 has a flatter aspherical curve, preferably by about 30%, than the top lens 80. The edges of the two lenses may be cemented together to form an air gap 82 or the two lenses may be mounted in an air tight tube. The outer face 84 of lens 80 is aspherical and the outer face 85 of lens 81 is also aspherical. In addition, if desired, the inner faces of those lenses may also be formed with aspherical shapes. The aspherical lens system is preferably small to facilitate the surgeon's manipulation of instruments around the cornea. That lens system preferably is light in weight and has a wide field of view.

In operation, the bottom lens 81 collects the image, for example from the periphery of the inner surface (retina area) of the eyeball during an eye operation. That image is reduced in size. The top lens 80 magnifies the reduced image and forms it in air, for example 10 mm–15 mm, above the lens surface 84.

However, the magnified image is inverted (left to right and right to left) relative to the object.

Figure 4B:
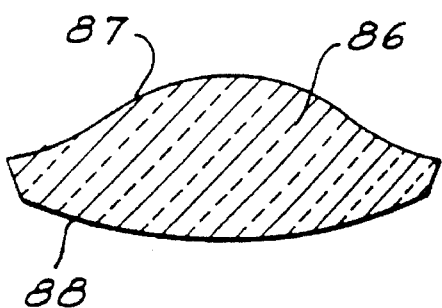
FIG. 4B is a side cross-sectional view showing an aspherical lens system comprised of a single solid lens.

An aspherical lens 86 ("aspherical lens system") made of a single solid lens is shown in FIG. 4B. Aspherical lens 86 has two oppositely facing convex surfaces that have aspherical shapes. The solid aspherical lens 86 functions similarly to the dual lens system. The bottom surface 88 collects the image from a wide field of view, such as the entire periphery of the inside of the eyeball, as well as the retina at the back of the eyeball. The top surface 87 magnifies the image produced by the bottom surface 88. The magnified image produced by the solid aspherical lens 86 is inverted relative to the object.

The use of either the single or dual aspherical lens system produces an image of great depth and a wide field of view. In eye surgery, the interior view of the eyeball is greatly expanded to show a full peripheral view of the sides of the eyeball as well as the back of the eyeball. The image produced also has a three-dimensional appearance that allows the surgeon to operate more accurately.

In FIG. 1 the inverter 14 is shown positioned above the zoom 15 (zoom optics). This has the advantages of relatively simpler engineering, relatively better access and less expense. It is out of the way of the surgeon and there is no need for a second objective lens. The disadvantages are that it requires a longer housing and requires, proximate the inverter, built-in filters 23 for protecting the user's eyes from diode laser beams.

Alternatively, and not shown, the inverter 14 may be located below the zoom lenses 15. This provides a shorter body length and does not interfere with the laser shutter. However, it may require a compensating objective lens so that, when the inverter is used, the focal point will be matched to the image (in air) of the aspherical lens system 30. However, this arrangement has a shorter focal distance to the eye, which may interfere with some instruments.

Figure 2:
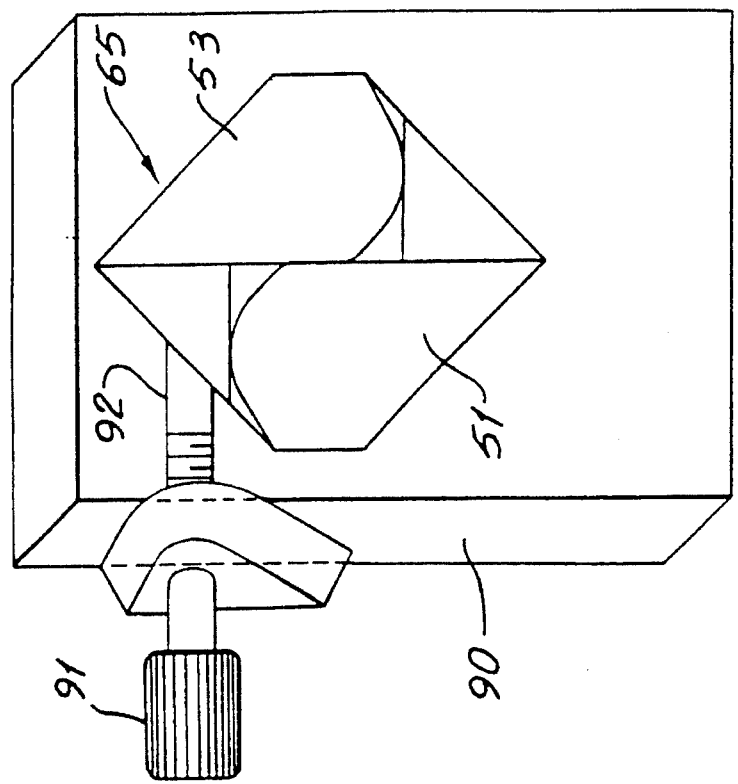
FIG. 2 is a perspective view, illustrating the inverted prism system within its enclosure.

The inverter 14 may be built into the housing 13. However, preferably, as shown in FIG. 2 the four prisms of the inverter are held in a frame (housing) 90 having knob 91 with a threaded (screws) shaft 92 to adjust the position of the prism assembly within the frame 90. The frame 90 slides, on rails, to be inserted into the housing 13 and may be removed so that the microscope may be used, with its normal stereoscopic view, for other purposes. For example, the frame 90 may be retracted for external eye surgery when the additional aspherical lens system (wide angle contact lens system) is not used.

Figure 5:
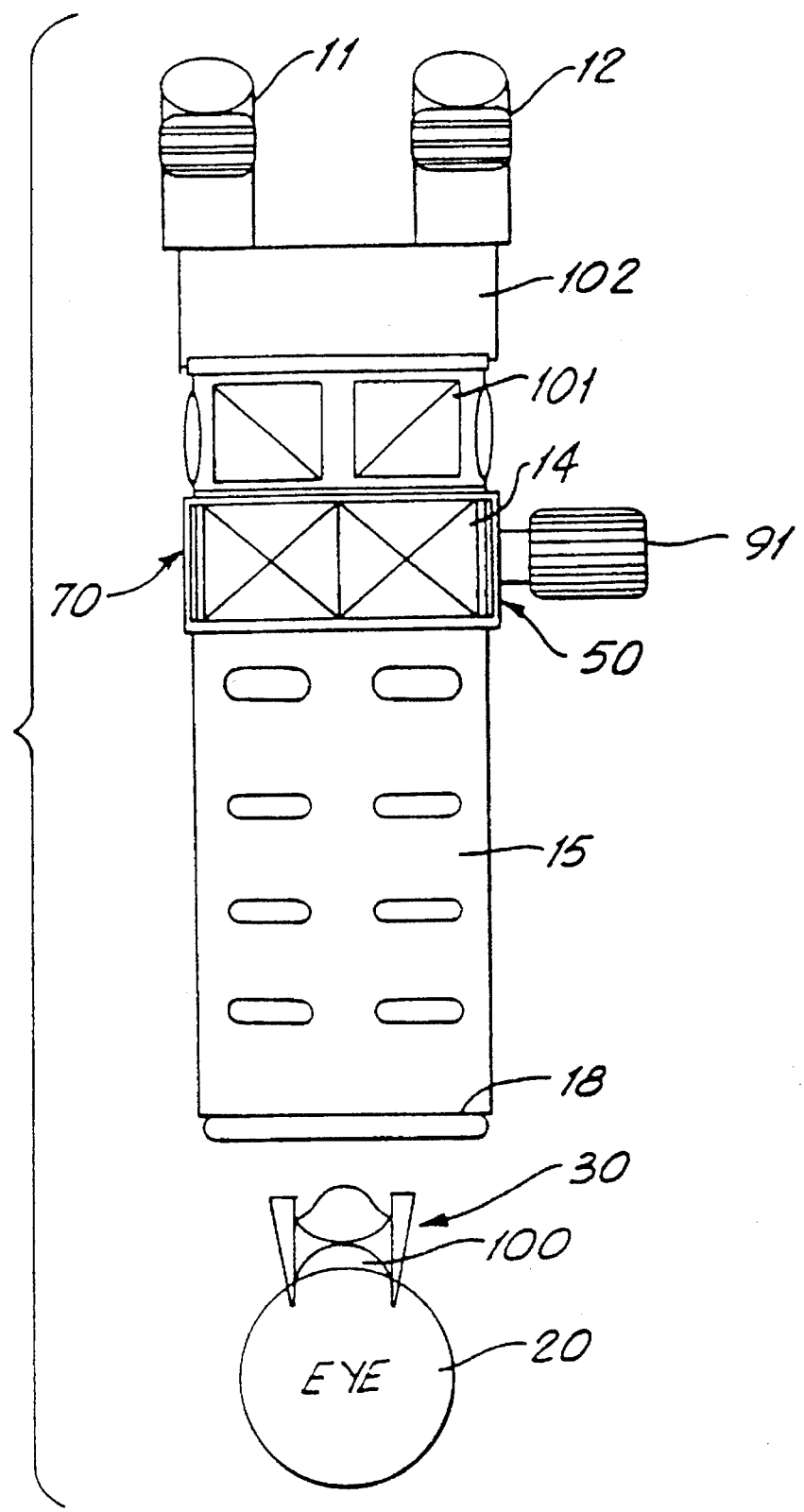
FIG. 5 is a front plan view of the optical stereoscopic system of the present invention.

As shown in FIG. 5, the eye 20 being operated upon has a cornea 100. The aspherical lens system 30 ("additional aspheric lens system") is proximate the cornea 100 and forms an image for the microscopic objective lens system 18. As shown in FIG. 6, the aspheric lens and the conformer lens 21 may be contained in a common housing which is used to position the eyeball. The zoom lens system (zoom optics) 15 is positioned beneath the inverter 14 and a beam splitter 101 is positioned above the inverter 14. The beam splitter 101 provides a stereo image to the optical system (not shown) for the surgeon's assistant or a stereo video camera. The binocular tubes 102 and eye piece lenses 11 and 12 are positioned above the beam splitter 101.

Figure 7:
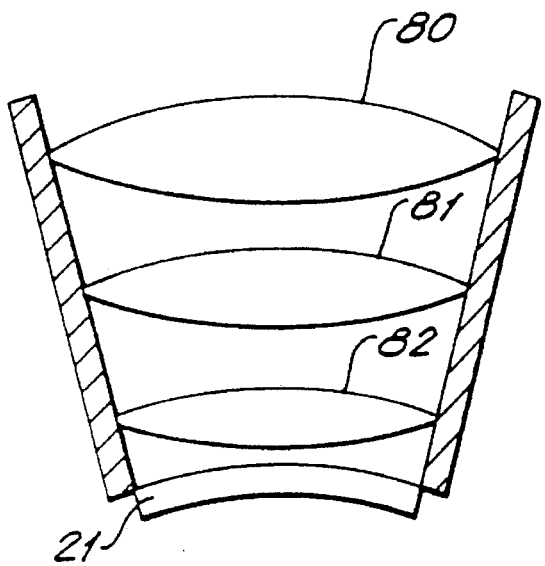
FIG. 7 is a side cross-sectional view showing a plastic aspherical lens system and a cornea conformer lens in a single housing.

Modifications may be made within the scope of the claims. For example, as shown in FIG. 7, the aspherical lens system having two convex surfaces consists of three plastic convex-convex lenses 80, 81, 82 each of which is aspherical. Preferably the plastic lens 80–82 and the conformer lens 21 are of the optical plastic PMMA (polymethacrylic).

I claim:

1. A stereoscopic microscope system adapted for vitrectomy eye microsurgery comprising:

(a) positioning means to position an eye to be viewed;

(b) an aspherical lens system located adjacent the positioning means and comprising a first lens having convex-concave curved faces proximate the positioning means and a second lens having concave-convex faces and facing the first lens, with the concave faces of the first and second lenses facing each other, the aspherical lens system producing a single inverted image;

(c) an image splitting means for splitting said inverted image from the aspherical lens system into separated left and right inverted images;

(d) a prism system means to re-invert said separated left and right images from the image splitting means, said prism system means consisting of four prisms constituting two pairs of prisms, each pair of prisms being an Abbe's Modification of Porro prism system, each of the said four prisms being the same size and shape, the four prisms being cemented together to form top and bottom layers of a unitary prism cluster; and the prism system means reverting said left and right inverted images to produce left and right reverted images; and (e) binocular tubes and eyepiece means for viewing said left and right reverted images.

2. The stereoscopic microscope system as in claim 1 wherein the image splitting means that produces separated left and right inverted images is an objective lens system of the stereomicroscope.

3. The stereoscopic microscope system as in claim 2 including a zoom lens magnification changer means positioned between the objective lens system and the prism system means, wherein such zoom lens magnification changer means reduces or enlarges the separated left and right inverted images from the objective lens system.

4. The stereoscopic microscope system as in claim 3 including a beam splitter means positioned between the zoom lens magnification changer means and the binocular tubes and eyepiece means, wherein such beam splitter means is used to split the left and right images from the zoom lens into primary left and right images and secondary left and right images.

5. The stereoscopic microscope system as in claim 2 including a zoom lens magnification changer means positioned adjacent the prism system means, wherein the zoom lens magnification changer means enlarges or reduces the separated left and right reverted images from the prism system.

6. The stereoscopic microscope system as in claim 2 including a beam splitter means positioned between the prism system means and the binocular tubes and eyepiece means, wherein the beam splitter means splits the left and right reverted images from the prism system into primary left and right reverted images, which are sent to the binocular tubes and eyepieces, and secondary left and right reverted images, which are sent to an auxiliary or secondary viewing port.

7. The stereoscopic microscope system as in claim 1 and including filters in the prism system to provide protection from laser beams.

8. A stereoscopic microscope system adapted for vitrectomy eye microsurgery comprising:

(a) positioning means to position an eye to be viewed;

(b) an aspherical lens system located adjacent the positioning means having two oppositely facing convex surfaces, the aspherical lens system producing a single inverted image;

(c) an image splitting means for splitting said inverted image from the aspherical lens system into separated left and right inverted images;

(d) a prism system means to re-invert said separated left and right images from the image splitting means, said prism system means consisting of four prisms constituting two pairs of prisms, each pair of prisms being an Abbe's Modification of Porro Prism system, each of the four prisms being the same size and shape, the four prisms being cemented together to form top and bottom layers of a unitary prism cluster, and the prism system means reverting said left and right inverted images to produce left and right reverted images; and (e) binocular tubes and eyepiece means for viewing said left and right reverted images.

9. The stereoscopic microscope system as in claim 8 wherein the aspherical lens system comprises a single lens and the positioning means comprises a convex-concave eyeball conformer lens.

10. The stereoscopic microscope system as in claim 8 wherein the image splitting means that produces separated left and right inverted images is an objective lens system of the stereomicroscope.

11. The stereoscopic microscope system as in claim 10 including a zoom leans magnification changer means positioned between the objective lens system and the prism system means, wherein such zoom lens magnification changer means reduces or enlarges the separated left and right inverted images from the objective lens system.

12. The stereoscopic microscope system as in claim 11 including a beam splitter means positioned between the zoom lens magnification changer means and the binocular tubes and eyepiece means, wherein such beam splitter means is used to split the left and right images from the zoom lens into primary left and right images and secondary left and right images.

13. The stereoscopic microscope system as in claim 10 including a zoom lens magnification changer means positioned adjacent the prism system means, wherein the zoom lens magnification changer means enlarges or reduces the separated left and right reverted images from the prism system means.

14. The stereoscopic microscope system as in claim 10 including a beam splitter means positioned between the prism system means and the binocular tubes and eyepiece means, wherein the beam splitter means splits the left and right reverted images from the prism system means into primary left and right reverted images which are sent to the binocular tubes and eyepiece means and secondary left and right reverted images which are sent to the binocular tubes and eyepieces, and secondary left and right reverted images which are sent to an auxiliary or secondary viewing port.

15. The stereoscopic microscope system as in claim 8 and including filters in the prism system means to provide protection from laser beams.

* * * * *